(12) United States Patent
Yamagata et al.

(10) Patent No.: US 10,080,534 B2
(45) Date of Patent: Sep. 25, 2018

(54) MEDICAL IMAGE DIAGNOSTIC DEVICE

(71) Applicant: Toshiba Medical Systems Corporation, Otawara-shi (JP)

(72) Inventors: Hitoshi Yamagata, Otawara (JP); Kazuya Okamoto, Saitama (JP); Takuzo Takayama, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 783 days.

(21) Appl. No.: 14/522,228

(22) Filed: Oct. 23, 2014

(65) Prior Publication Data

US 2015/0065861 A1 Mar. 5, 2015

Related U.S. Application Data

(63) Continuation of application No. PCT/JP2013/062130, filed on Apr. 24, 2013.

(30) Foreign Application Priority Data

Apr. 24, 2012 (JP) .................................. 2012-099037

(51) Int. Cl.
*A61B 6/00* (2006.01)
*A61B 5/055* (2006.01)
(Continued)

(52) U.S. Cl.
CPC .......... *A61B 6/4417* (2013.01); *A61B 5/0035* (2013.01); *A61B 5/055* (2013.01);
(Continued)

(58) Field of Classification Search
CPC ... A61B 6/4417; A61B 6/4476; A61B 5/0035; A61B 5/0555; A61B 6/037; A61B 6/032;
(Continued)

(56) References Cited

U.S. PATENT DOCUMENTS 8,073,527 B2 * 12/2011 Eberler .............. G01R 33/3415
250/363.03
2007/0055127 A1 3/2007 Ladebeck et al.
(Continued)

FOREIGN PATENT DOCUMENTS

JP 09-024035 A 1/1997
JP 2008-149147 A 7/2008
(Continued)

OTHER PUBLICATIONS

U.S. Appl. No. 14/522,024, filed Oct. 23, 2014, Okamoto, et al.
(Continued)

*Primary Examiner* — Sanjay Cattungal
(74) *Attorney, Agent, or Firm* — Oblon, McClelland, Maier & Neustadt, L.L.P.

(57) ABSTRACT

A medical image diagnostic device according to an embodiment includes a first collector, a second collector, and an image generator. The first collector collects data from a first region of a subject through a first detector. The second collector collects data from a second region of the subject that is different from the first region through a second detector. The image generator generates a first diagnostic image from the data collected by the first collector and generates a second diagnostic image from the data collected by the second collector.

11 Claims, 13 Drawing Sheets

(51) Int. Cl.
  *A61B 6/03* (2006.01)
  *A61K 49/04* (2006.01)
  *G01R 33/48* (2006.01)
  *G01T 1/29* (2006.01)
  *G01T 1/16* (2006.01)
  *G01T 1/161* (2006.01)
  *A61B 5/00* (2006.01)
  *A61B 6/04* (2006.01)

(52) U.S. Cl.
  CPC ............ *A61B 5/0555* (2013.01); *A61B 6/032* (2013.01); *A61B 6/037* (2013.01); *A61B 6/4476* (2013.01); *A61K 49/04* (2013.01); *G01R 33/481* (2013.01); *G01T 1/1603* (2013.01); *G01T 1/1611* (2013.01); *G01T 1/2985* (2013.01); *A61B 5/0042* (2013.01); *A61B 6/0407* (2013.01); *A61B 6/0457* (2013.01); *A61B 6/4266* (2013.01); *A61B 6/501* (2013.01); *A61B 6/507* (2013.01); *A61B 6/54* (2013.01); *A61B 2576/026* (2013.01)

(58) Field of Classification Search
  CPC ......... A61B 5/055; A61B 6/507; A61B 6/501; A61B 6/4266; A61B 6/0407; A61B 6/54; A61B 6/0457; A61B 5/0042; A61B 2576/026; G01T 1/1611; G01T 1/1603; G01T 1/2985; A61K 49/04; G01R 33/481
  USPC .................................................. 600/407–436
  See application file for complete search history.

(56) References Cited

U.S. PATENT DOCUMENTS

| | | | |
|---|---|---|---|
| 2007/0102641 A1 | 5/2007 | Schmand et al. | |
| 2008/0146914 A1* | 6/2008 | Polzin | A61B 5/055 600/420 |
| 2011/0031407 A1 | 2/2011 | Yamaya et al. | |
| 2011/0224534 A1* | 9/2011 | Yamaya | G01R 33/481 600/411 |
| 2012/0150017 A1* | 6/2012 | Yamaya | G01R 33/3806 600/411 |
| 2013/0234710 A1 | 9/2013 | Kanno et al. | |
| 2013/0241555 A1 | 9/2013 | Obata et al. | |
| 2013/0296689 A1 | 11/2013 | Okamoto et al. | |
| 2013/0324836 A1 | 12/2013 | Yamaya et al. | |
| 2015/0065854 A1* | 3/2015 | Ahn | A61B 6/5247 600/411 |

FOREIGN PATENT DOCUMENTS

| | | |
|---|---|---|
| JP | 2008-525161 A | 7/2008 |
| JP | 2011-185796 A | 9/2011 |
| WO | WO 2009/133628 A1 | 11/2009 |
| WO | WO 2010/103644 A1 | 9/2010 |

OTHER PUBLICATIONS

International Search Report dated Aug. 6, 2013 for PCT/JP2013/062130 filed Apr. 24, 2013 with English Translation.

International Written Opinion dated Aug. 6, 2013 for PCT/JP2013/062130 filed Apr. 24, 2013.

U.S. Appl. No. 13/873,706, filed Apr. 30, 2013, 2013-0234710, Kanno, et al.

U.S. Appl. No. 13/874,795, filed May 1, 2013, 2013-0241555, Obata, et al.

U.S. Appl. No. 13/938,592, filed Jul. 10, 2013, 2013-0324836, Yamaya, et al.

U.S. Appl. No. 13/935,812, filed Jul. 5, 2013, 2013-0296689, Okamoto, et al.

* cited by examiner

MEDICAL IMAGE DIAGNOSTIC DEVICE

CROSS-REFERENCE TO RELATED APPLICATIONS

This application is a continuation of PCT international application Ser. No. PCT/JP2013/062130 filed on Apr. 24, 2013 which designates the United States, and which claims the benefit of priority from Japanese Patent Application No. 2012-099037, filed on Apr. 24, 2012; the entire contents of which are incorporated herein by reference.

FIELD

Embodiments described herein relate to a medical image diagnostic device.

BACKGROUND

Conventionally, in medical practice such as hospitals, image diagnosis by using medical image diagnostic devices such as a magnetic resonance imaging (MRI) device, an X-ray computed tomography (CT) device, and a positron emission tomography (PET) device has been performed widely. In recent years, multiple medical image diagnostic devices such as a PET-CT device as a combination of the PET device and the X-ray CT device and a PET-MRI device as a combination of the PET device and the MRI device have been also put into production.

DETAILED DESCRIPTION

A medical image diagnostic device according to an embodiment includes a first collector, a second collector, and an image generator. The first collector collects data from a first region of a subject through a first detector. The second collector collects data from a second region of the subject that is different from the first region through a second detector. The image generator generates a first diagnostic image from the data collected by the first collector and generates a second diagnostic image from the data collected by the second collector.

Hereinafter, described are embodiments of a medical image diagnostic device with reference to the accompanying drawings. Hereinafter, described is an embodiment of a PET-MRI device as a first embodiment. Furthermore, described is an embodiment of a PET-CT device as a second embodiment.

First Embodiment

Figure 1:
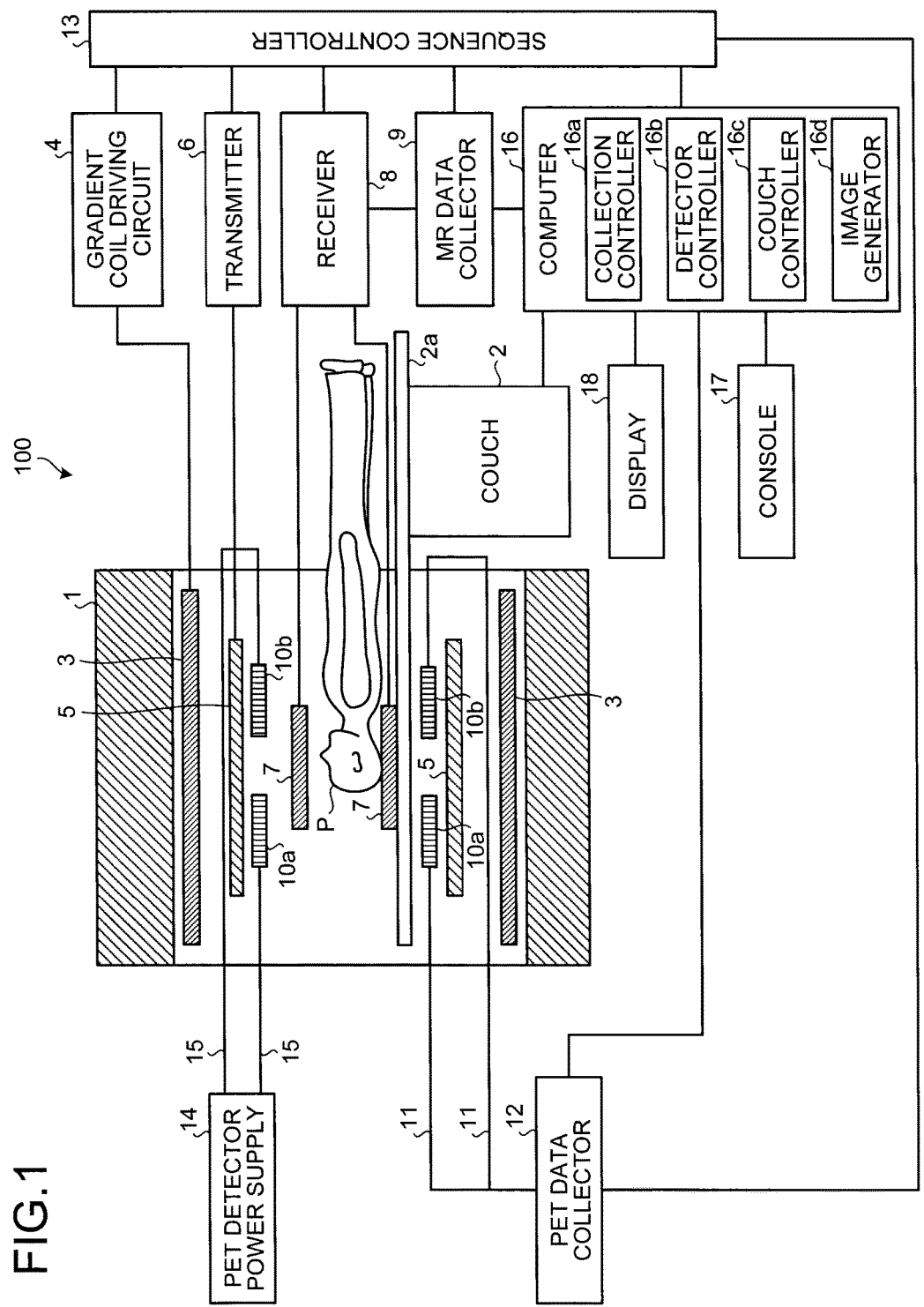
FIG. 1 is a view illustrating a configuration of a PET-MRI device according to a first embodiment.

First, described is the first embodiment. FIG. 1 is a view illustrating a configuration of the PET-MRI device according to the first embodiment. As illustrated in FIG. 1, a PET-MRI device 100 includes a static magnetic field magnet 1, a couch 2, a gradient coil 3, a gradient coil driving circuit 4, a transmitting high-frequency coil 5, a transmitter 6, receiving high-frequency coil 7, a receiver 8, a magnetic resonance (MR) data collector 9, PET detectors 10a and 10b, signal lines 11, a PET data collector 12, a sequence controller 13, a PET detector power supply 14, power supply cables 15, a computer 16, a console 17, and a display 18.

The static magnetic field magnet 1 generates a static magnetic field in a substantially cylindrical bore. The bore is a space formed as an inner wall of a substantially cylindrical gantry accommodating the static magnetic field magnet 1, the gradient coil 3, and the like. Hereinafter, the inner wall forming the bore is referred to as a bore inner wall. The couch 2 includes a couchtop 2a on which a subject P is placed. The couch 2 moves the couchtop 2a into the bore at the time of imaging so as to move the subject P into the static magnetic field.

The gradient coil 3 applies gradient magnetic fields Gx, Gy, and Gz to the subject P. In the gradient magnetic fields Gx, Gy, and Gz, magnetic field strengths in the same direction (Z direction) as the static magnetic field change substantially linearly with respect to distances from the center of the magnetic field in the X, Y, and Z directions. The gradient coil 3 is formed into a substantially cylindrical form and is arranged at the inner circumferential side of the static magnetic field magnet 1. The gradient coil driving circuit 4 drives the gradient coil 3 under the control of the sequence controller 13.

The transmitting high-frequency coil 5 applies a high-frequency magnetic field to the subject P placed in the static magnetic field based on a high-frequency pulse transmitted from the transmitter 6. The transmitting high-frequency coil 5 is formed into a substantially cylindrical form and is arranged at the inner circumferential side of the gradient coil 3. The transmitter 6 transmits the high-frequency pulse to the transmitting high-frequency coil 5 under the control of the sequence controller 13.

The receiving high-frequency coil 7 detects a magnetic resonance signal emitted from the subject P by application of the high-frequency magnetic field and the gradient magnetic field. For example, the receiving high-frequency coil 7 is a surface coil arranged on the surface of the subject P in accordance with a site to be imaged. For example, when a body portion of the subject P is imaged, two receiving high-frequency coils 7 are arranged at the upper and lower side of the subject. The receiver 8 receives the magnetic resonance signal detected by the receiving high-frequency coil 7 under the control of the sequence controller 13. Then, the receiver 8 transmits the received magnetic resonance signal to the MR data collector 9.

The MR data collector 9 collects MR data through the receiving high-frequency coil 7. To be more specific, the MR data collector 9 amplifies and detects the magnetic resonance signal transmitted from the receiver 8, and then, A-to-D-converts it so as to collect the MR data. Then, the MR data collector 9 transmits the collected MR data to the computer 16.

The PET detectors 10a and 10b detect gamma rays emitted from a positron-emitting radionuclide administered to the subject P as count information. These PET detectors 10a and 10b are formed into ring forms and are arranged at the inner circumferential side of the transmitting high-frequency coil 5. Then, the PET detectors 10a and 10b transmit the detected count information to the PET data collector 12 through the signal lines 11.

For example, each of the PET detectors 10a and 10b is formed by arranging detector modules each having a scintillator and an optical detector in a ring form. The scintillator is a lutetium yttrium oxyorthosilicate (LYSO), a lutetium oxyorthosilicate (LSO) or a lutetium gadolinium oxyorthosilicate (LGSO), for example. Furthermore, the optical detector is a semiconductor detector such as an avalanche photodiode (APD) element and a silicon photomultiplier (SiPM) or a photomultiplier tube (PMT), for example.

Figure 2:
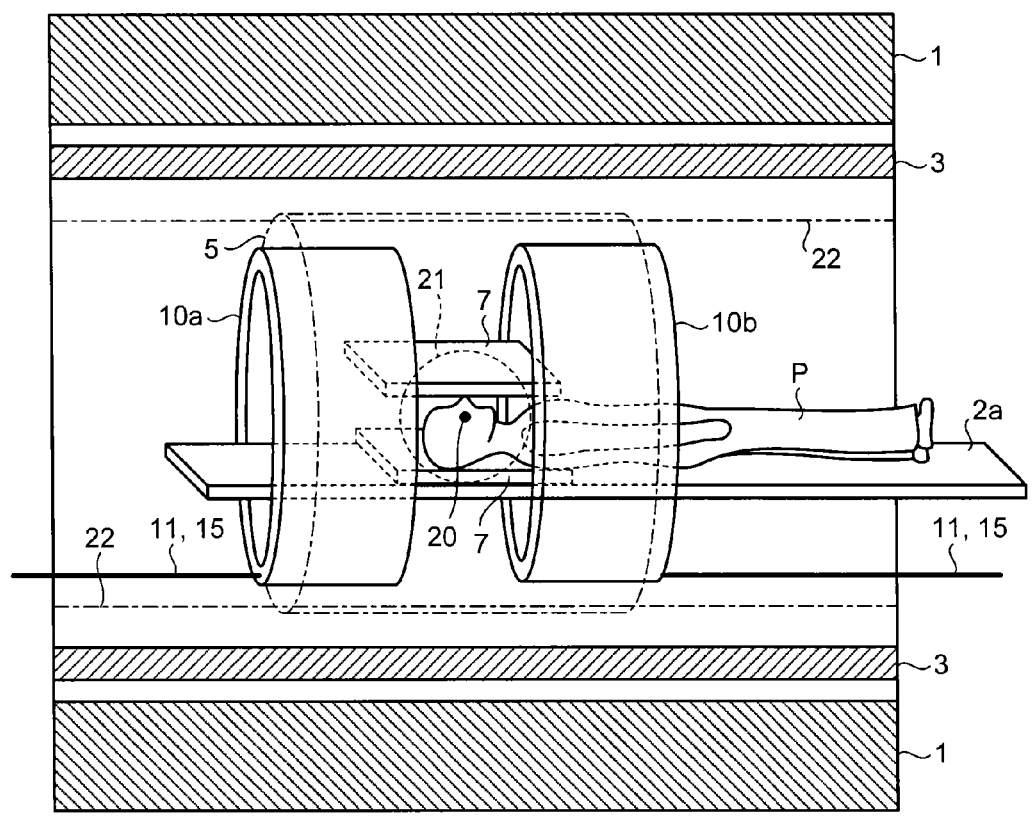
FIG. 2 is a view illustrating the arrangement of parts around PET detectors in the first embodiment.

Then, described is the arrangement of the PET detectors 10a and 10b in the first embodiment. FIG. 2 is a view illustrating the arrangement of parts around the PET detectors 10a and 10b in the first embodiment. In FIG. 2, a point 20 indicates the magnetic field center of the static magnetic field and a spherical region 21 surrounded by a dotted line indicates an effective imaging region of an MR image. As illustrated in FIG. 2, the PET detectors 10a and 10b are arranged at the inner circumferential side of a bore inner wall 22, for example.

Figure 3:
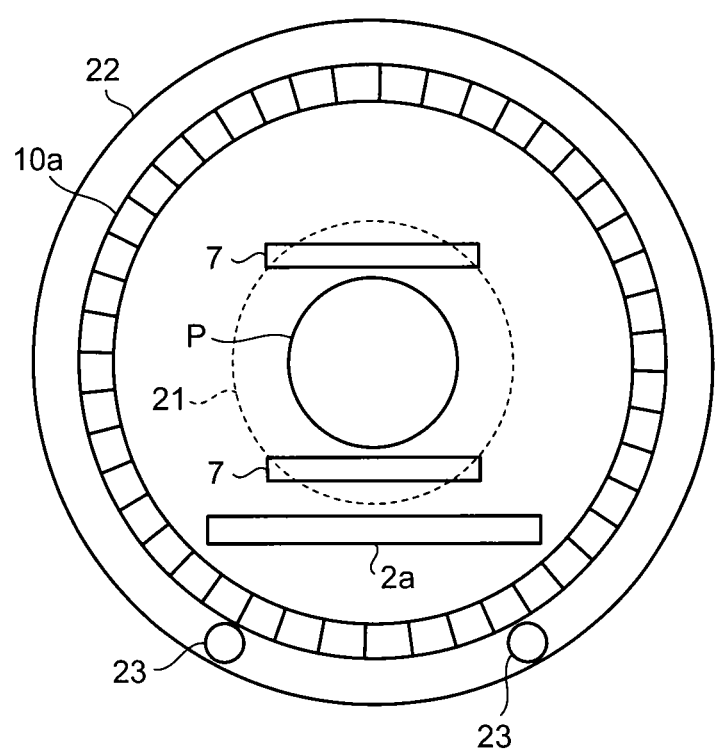
FIG. 3 is a view for explaining movement mechanisms of the PET detectors in the first embodiment.

The PET detectors 10a and 10b are provided so as to be movable in an axial direction of the bore and are moved by movement mechanisms. FIG. 3 is a view for explaining the movement mechanisms of the PET detectors 10a and 10b in the first embodiment. FIG. 3 illustrates the arrangement of the parts around the PET detectors 10a and 10b when seen from the axial direction of the bore. To be more specific, FIG. 3 illustrates the arrangement of the parts when the inner portion of the bore is seen from an opening at the side at which the PET detector 10a is arranged.

As illustrated in FIG. 3, the PET-MRI device 100 includes movement mechanisms 23 for moving the PET detector 10a along the axial direction of the bore. The movement mechanisms 23 move the PET detector 10a along the axial direction of the bore under the control of the computer 16.

For example, the movement mechanisms 23 are two rails installed on a lower portion of the bore inner wall 22. The movement mechanisms 23 are fitted into rail bearings formed on the outer circumferential surface of the PET detector 10a in groove forms. The movement mechanisms 23 support the PET detector 10a so as to be movable along the axial direction of the bore. The movement mechanisms 23 for moving the PET detector 10b are also provided at the side of the PET detector 10b in the same manner.

Figure 4:
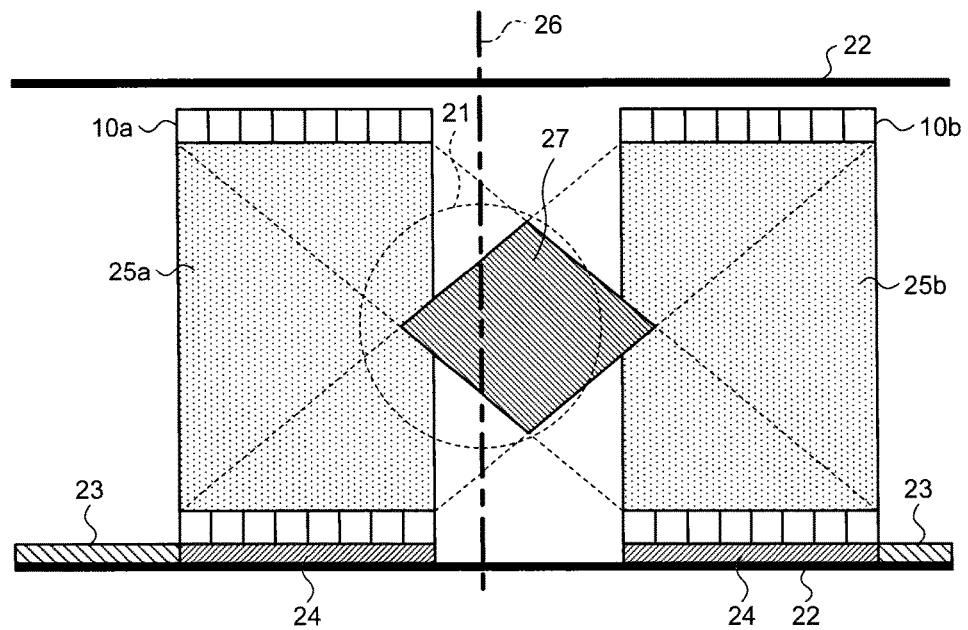
FIG. 4 is a view illustrating effective imaging regions in the PET-MRI device in the first embodiment.

In the PET-MRI device 100 according to the embodiment, the above-mentioned PET detectors 10a and 10b set effective imaging regions for capturing PET images. FIG. 4 is a view illustrating the effective imaging regions in the PET-MRI device 100 in the first embodiment. It is to be noted that in FIG. 4, a dashed line 26 indicates the center position in the axial direction of the bore.

As illustrated in FIG. 4, in the PET-MRI device 100, the MR imaging region 21 as the effective imaging region of the MR image is set in the vicinity of the center in the axial direction of the bore. The MR imaging region 21 is a spherical region defined in accordance with uniformity of the magnetic field and is a region in which equal to or higher than constant image quality and less constant image strain are guaranteed.

Furthermore, in the PET-MRI device 100, a first PET imaging region 25a, a second PET imaging region 25b, and a third PET imaging region 27 as effective regions for capturing the PET images are set. The first PET imaging region 25a is a region surrounded by the inner circumferential surface of the PET detector 10a. The second PET imaging region 25b is a region surrounded by the inner circumferential surface of the PET detector 10b.

The third PET imaging region 27 is a region obtained by rotating an intersecting portion of an X-shaped region formed between the inner circumferential surface of the PET detector 10a and the inner circumferential surface of the PET detector 10b on a plane passing through the center axis of the PET detectors 10a and 10b once while setting the center axis to a rotating center. The third PET imaging region 27 is a region having a shape obtained by bonding bottom surfaces of circular cones. The gamma rays emitted from the third PET imaging region 27 are detected by using two PET detectors so as to be detected with high possibility.

The lengths of the first PET imaging region 25a, the second PET imaging region 25b, and the third PET imaging region 27 as described above in the direction perpendicular to the axial direction of the bore are changed and their sizes are changed by moving the PET detectors 10a and 10b. The PET detectors 10a and 10b are moved by the movement mechanisms 23 and vibration from the gradient coil 3 is reduced by vibration damping mechanisms 24.

As described above, in the PET-MRI device 100 according to the first embodiment, four effective imaging regions including the MR imaging region 21, the first PET imaging region 25a, the second PET imaging region 25b, and the third PET imaging region 27 are set. In the PET-MRI device 100, a plurality of regions of a subject that are diagnostic targets are arranged in the respective effective imaging regions, so that data can be collected for each lesion site of equal to or more than one lesion site in the subject P.

For example, the PET detector 10a and the PET detector 10b are arranged so as to be asymmetric to each other with respect to the center defined in the PET-MRI device 100. To be more specific, as illustrated in FIG. 4, the PET detector 10a and the PET detector 10b are arranged so as to be asymmetric to each other with respect to the center of the magnetic field defined in the PET-MRI device 100. Furthermore, as illustrated in FIG. 4, the PET detector 10a and the PET detector 10b are arranged so as to be asymmetric to each other in the body axis direction of the subject. The body axis direction of the subject corresponds to the axial direction (Z-axis direction) of the bore normally.

In this case, the first PET imaging region 25a and the second PET imaging region 25b are arranged so as to be asymmetric to each other with respect to the center defined in the PET-MRI device 100. To be more specific, as illustrated in FIG. 4, the first PET imaging region 25a and the second PET imaging region 25b are arranged so as to be asymmetric to each other with respect to the center of the magnetic field defined in the PET-MRI device 100. Furthermore, as illustrated in FIG. 4, the first PET imaging region 25a and the second PET imaging region 25b are arranged so as to be asymmetric to each other in the body axis direction of the subject.

When the receiving high-frequency coil 7 has a plurality of coil elements aligned in the horizontal direction (X-axis direction), the coil elements can be divided into a plurality of sections in the horizontal direction and a part of the sections can be used for data collection. In this case, a section of the coil element to be used for data collection and the respective PET detectors are arranged so as to be asymmetric in the horizontal direction. In other words, in the PET-MRI device 100, the coil element receiving the magnetic resonance signal and the PET detectors detecting the gamma rays can be arranged so as to be asymmetric in the horizontal direction.

In this case, the MR imaging region and the respective PET imaging regions are arranged so as to be asymmetric in the horizontal direction with respect to the axis of the bore. The MR imaging region can be also deviated in the horizontal direction by moving the couchtop 2a without using the section of the part of the coil elements included in the receiving high-frequency coil 7. With this, the MR imaging region and the respective PET imaging regions can be arranged so as to be asymmetric in the horizontal direction with respect to the axis of the bore.

Furthermore, the MR imaging region can be also deviated in the up-down direction by exciting a part of the subject P in the up-down direction locally. This makes it possible to arrange the MR imaging region and the respective PET imaging regions so as to be asymmetric in the up-down direction with respect to the axis of the bore. That is to say, in the PET-MRI device 100, the MR imaging region and the respective PET imaging regions can be arranged so as to be asymmetric in all the directions of the X-axis direction, the Y-axis direction, and the Z-axis direction with respect to the axis of the bore.

Furthermore, in the embodiment, as illustrated in FIG. 4, the MR imaging region 21 and the third PET imaging region 27 are set such that a portion of the MR imaging region 21 and a portion of the third PET imaging region 27 are overlapped. In other words, the MR imaging region 21 is set such that a portion thereof is not overlapped with the third PET imaging region 27 and the third PET imaging region 27 is set such that a portion thereof is not overlapped with the MR imaging region 21. That is to say, the overall MR imaging region 21 is not encompassed by the third PET imaging region 27, and the overall third PET imaging region 27 is not encompassed by the MR imaging region 21 conversely.

In the same manner, for example, as illustrated in FIG. 4, the MR imaging region 21 and the first PET imaging region 25a are set such that a portion of the MR imaging region 21 and a portion of the first PET imaging region 25a are overlapped. For example, as illustrated in FIG. 4, the first PET imaging region 25a and the third PET imaging region 27 are set such that a portion of the first PET imaging region 25a and a portion of the third PET imaging region 27 are overlapped. Furthermore, the second PET imaging region 25b and the third PET imaging region 27 are set such that a portion of the second PET imaging region 25b and a portion of the third PET imaging region 27 are overlapped.

Returning to the explanation of FIG. 1, the PET data collector 12 collects coincidence data through the PET detectors 10a and 10b. To be more specific, the PET data collector 12 generates combined data of pieces of count information obtained by detecting the gamma rays (including annihilation radiation) emitted from the positron-emitting radionuclide at substantially the same time by using the pieces of count information of the gamma rays detected by the PET detectors 10a and 10b so as to collect the coincidence data. Then, the PET data collector 12 transmits the collected coincidence data to the computer 16.

The sequence controller 13 controls the above-mentioned parts based on various types of imaging sequences set by the computer 16.

The PET detector power supply 14 supplies electric power for driving the optical detectors to the PET detectors 10a and 10b through the power supply cables 15.

The computer 16 controls the PET-MRI device 100 overall. The computer 16 includes the console 17 and the display 18. The console 17 receives various types of operations from an operator. The display 18 displays various types of information such as a medical image and a graphical user interface (GUI). The computer 16 includes a central processing unit (CPU) and a memory that execute various types of programs so as to execute various types of processing. Furthermore, the computer 16 includes a collection controller 16a, a detector controller 16b, a couch controller 16c, and an image generator 16d. These functional units are operated by executing various types of programs on the above-mentioned CPU and memory.

The collection controller 16a controls the MR data collector 9 and the PET data collector 12 in accordance with a direction from the operator. For example, the collection controller 16a controls the MR data collector 9 and the PET data collector 12 to start data collection at the same time. Alternatively, for example, the collection controller 16a controls them such that the PET data collector 12 starts data collection after a predetermined time has elapsed since the MR data collector 9 started data collection.

The detector controller 16b controls the movement of the PET detectors 10a and 10b. To be more specific, the detector controller 16b operates the movement mechanisms 23 so as to move the PET detectors 10a and 10b in the axial direction of the bore.

The couch controller 16c controls the operation of the couch 2 on which the subject P is placed. For example, the couch controller 16c controls the couch 2 so as to move the couchtop 2a on which the subject P is placed in the axial direction of the bore.

The image generator 16d generates an MR diagnostic image from the MR data collected by the MR data collector 9 and generates a PET diagnostic image from the coincidence data collected by the PET data collector 12. Then, the image generator 16d displays the generated MR diagnostic image and PET diagnostic image on the display 18.

For example, the image generator 16d generates a functional image such as a diffusion weighted imaging (DWI) image, a perfusion weighted imaging (PWI) image, and a functional MRI (fMRI) image or a morphological image such as a T1 weighted (T1W) image, a T2 weighted (T2W) image, and an MR angiography (MRA) image as the MR diagnostic image. Furthermore, the image generator 16d generates a functional image such as a metabolic imaging image and a molecular imaging image targeted on a specific biomarker as the PET diagnostic image.

In this manner, the image generator 16d generates various types of diagnostic images so as to generate a diagnostic image suitable to diagnosis of each lesion site of equal to or more than one lesion site in the subject P. The diagnosis herein indicates observation of vascular reaction and metabolic reaction on the lesion site, for example. For example, the vascular reaction can be observed by using the morphological image as the diagnostic image. Furthermore, the metabolic reaction can be observed by using the functional image as the diagnostic image.

Figure 5:
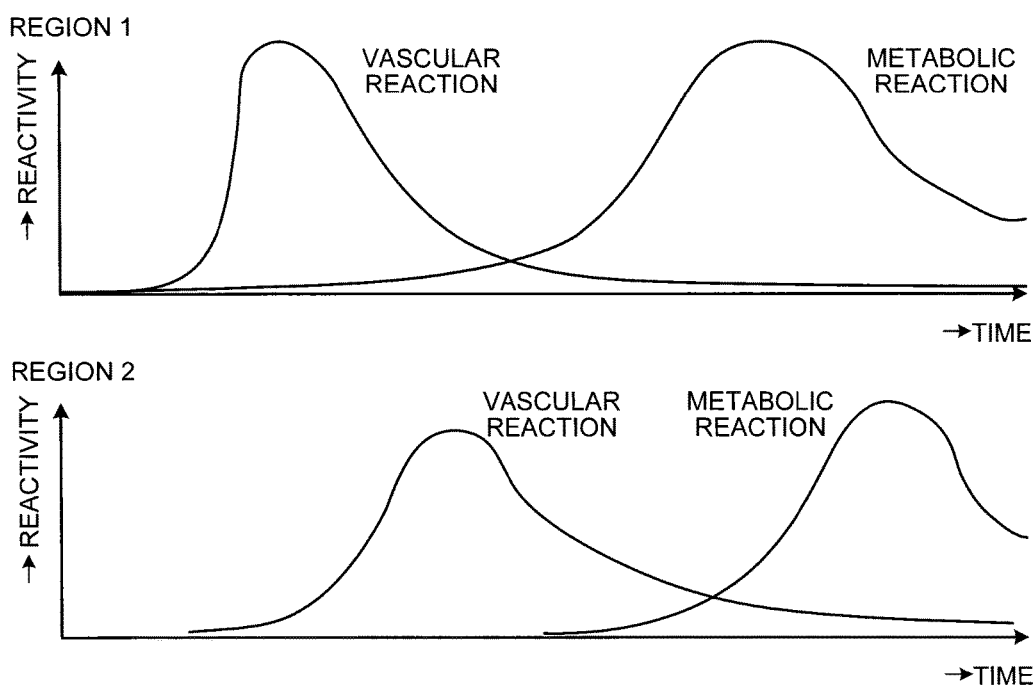
FIG. 5 is a view for explaining vascular reaction and metabolic reaction on two regions.

FIG. 5 is a view for explaining the vascular reaction and the metabolic reaction on two regions. As illustrated in the upper graph in FIG. 5, the vascular reaction and the metabolic reaction are different in the time reactivity. After a drug was administered to the subject P, the vascular reaction reaches a peak first, and then, the metabolic reaction reaches a peak. The vascular reaction and the metabolic reaction are observed for a plurality of regions, so that a disease relating to equal to or more than one lesion site can be diagnosed. Furthermore, the lower graph in FIG. 5 indicates the vascular reaction and the metabolic reaction on a region different from that in the upper graph in FIG. 5. For example, the vascular reaction is different temporally and qualitatively depending on the regions.

Described has been the configuration of the PET-MRI device 100 according to the embodiment above. With this configuration, the PET-MRI device 100 according to the embodiment can generate a diagnostic image for each lesion site of equal to or more than one lesion site in the subject P. Hereinafter, described in detail by using specific diagnostic examples are the functions of the PET-MRI device 100.

As a first diagnosis example, described is the case where the vascular reaction on a cerebrovascular region is observed with the MR diagnostic image, the vascular reactions on the parietal region, the cervical region and the abdominal region are observed with the PET diagnostic images, and the metabolic reactions on the parietal region, the cervical region and the abdominal region are observed with the PET diagnostic images.

Figure 6:
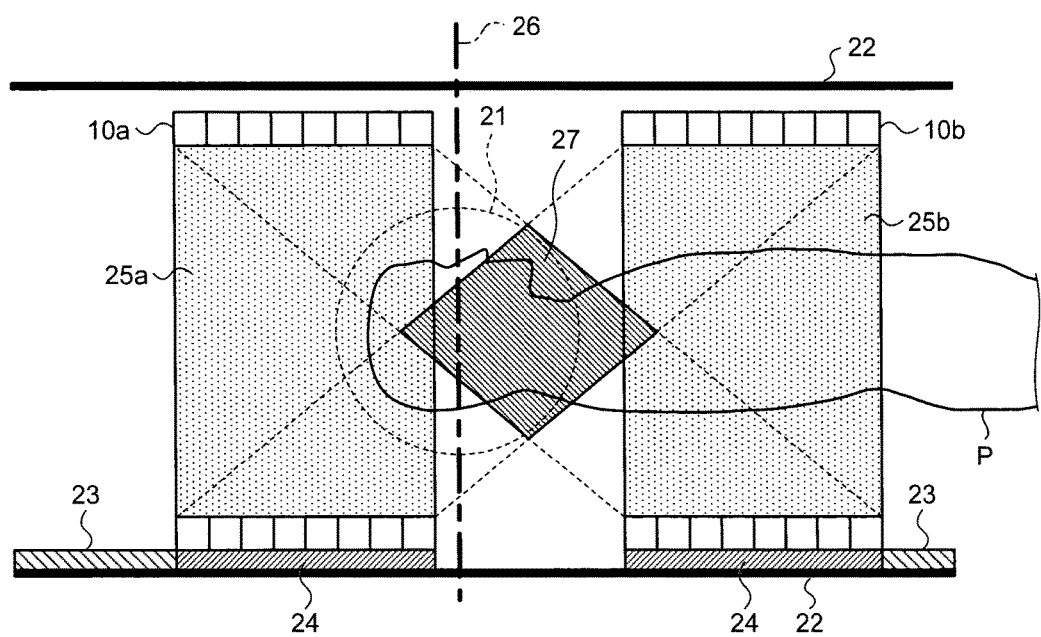
FIG. 6 is a view illustrating the arrangement of a subject in a first diagnosis example.
Figure 7:
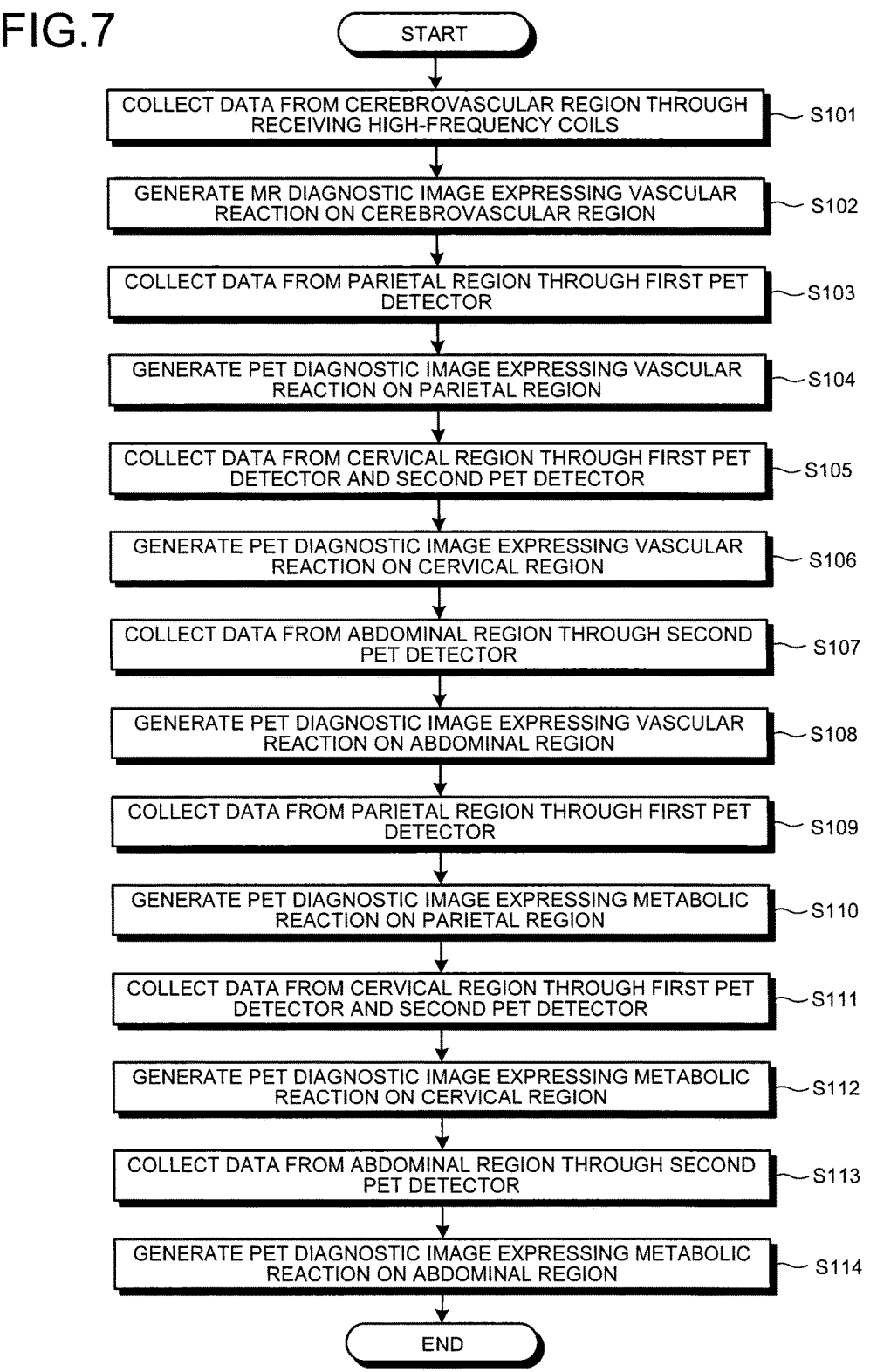
FIG. 7 is a flowchart illustrating the procedure of imaging of diagnostic images in the first diagnosis example.

FIG. 6 is a view illustrating the arrangement of the subject P in the first diagnosis example. FIG. 7 is a flowchart illustrating the procedure of imaging of the diagnostic images in the first diagnosis example. It is to be noted that in the flowchart as illustrated in FIG. 7, the PET detector 10a is expressed as the first PET detector and the PET detector 10b is expressed as the second PET detector.

As illustrated in FIG. 6, in the first diagnosis example, the subject P is arranged on the PET-MRI device 100 such that the overall cerebrovascular region is included in the MR imaging region 21, the parietal portion is included in the first PET imaging region 25a, the cervical portion is included in the third PET imaging region 27, and the abdominal portion is included in the second PET imaging region 25b.

As illustrated in FIG. 7, first, the MR data collector 9 collects data from the cerebrovascular region through the receiving high-frequency coil 7 (step S101). Then, the image generator 16d generates an MR diagnostic image expressing the vascular reaction on the cerebrovascular region from the data collected by the MR data collector 9 (step S102). For example, the image generator 16d generates a PWI image. With this, the operator can observe the vascular reaction on the cerebrovascular region.

Furthermore, the PET data collector 12 collects data from the parietal region through the PET detector 10a (step S103). Then, the image generator 16d generates a PET diagnostic image expressing the vascular reaction on the parietal region from the data collected by the PET data collector 12 (step S104). With this, the operator can observe the vascular reaction on the parietal region.

Subsequently, the PET data collector 12 collects data from the cervical region through the PET detectors 10a and 10b (step S105). Then, the image generator 16d generates a PET diagnostic image expressing the vascular reaction on the cervical region from the data collected by the PET data collector 12 (step S106). With this, the operator can observe the vascular reaction on the cervical region.

Furthermore, the PET data collector 12 collects data from the abdominal region through the PET detector 10b (step S107). Then, the image generator 16d generates a PET diagnostic image expressing the vascular reaction on the abdominal region from the data collected by the PET data collector 12 (step S108). With this, the operator can observe the vascular reaction on the abdominal region.

Thereafter, the PET data collector 12 collects data from the parietal region through the PET detector 10a (step S109). Then, the image generator 16d generates a PET diagnostic image expressing the metabolic reaction on the parietal region from the data collected by the PET data collector 12 (step S110). With this, the operator can observe the metabolic reaction on the parietal region.

Furthermore, the PET data collector 12 collects data from the cervical region through the PET detectors 10a and 10b (step S111). Then, the image generator 16d generates a PET diagnostic image expressing the metabolic reaction on the cervical region from the data collected by the PET data collector 12 (step S112). With this, the operator can observe the metabolic reaction on the cervical region.

Moreover, the PET data collector 12 collects data from the abdominal region through the PET detector 10b (step S113). Then, the image generator 16d generates a PET diagnostic image expressing the metabolic reaction on the abdominal region from the data collected by the PET data collector 12 (step S114). With this, the operator can observe the metabolic reaction on the abdominal region.

In the first diagnosis example, in the state where the positions of the PET detectors 10a and 10b are fixed, the diagnostic images for observing the vascular reactions on the cerebrovascular region, the parietal region, the cervical region and the abdominal region are generated, and then, the diagnostic images for observing the metabolic reactions on the parietal region, the cervical region and the abdominal region are generated. The collection controller 16a controls the above-mentioned operations of the MR data collector 9 and the PET data collector 12. The MR data collector 9 and the PET data collector 12 may start data collection at the same time or may start data collection at different timings.

Next, as a second diagnosis example, described is the case where the vascular reaction on the cerebrovascular region is observed with the MR diagnostic image, the vascular reactions on the cervical region and the abdominal region are observed with the PET diagnostic images, and the metabolic reaction on the head region is observed with the PET diagnostic image.

Figure 8:
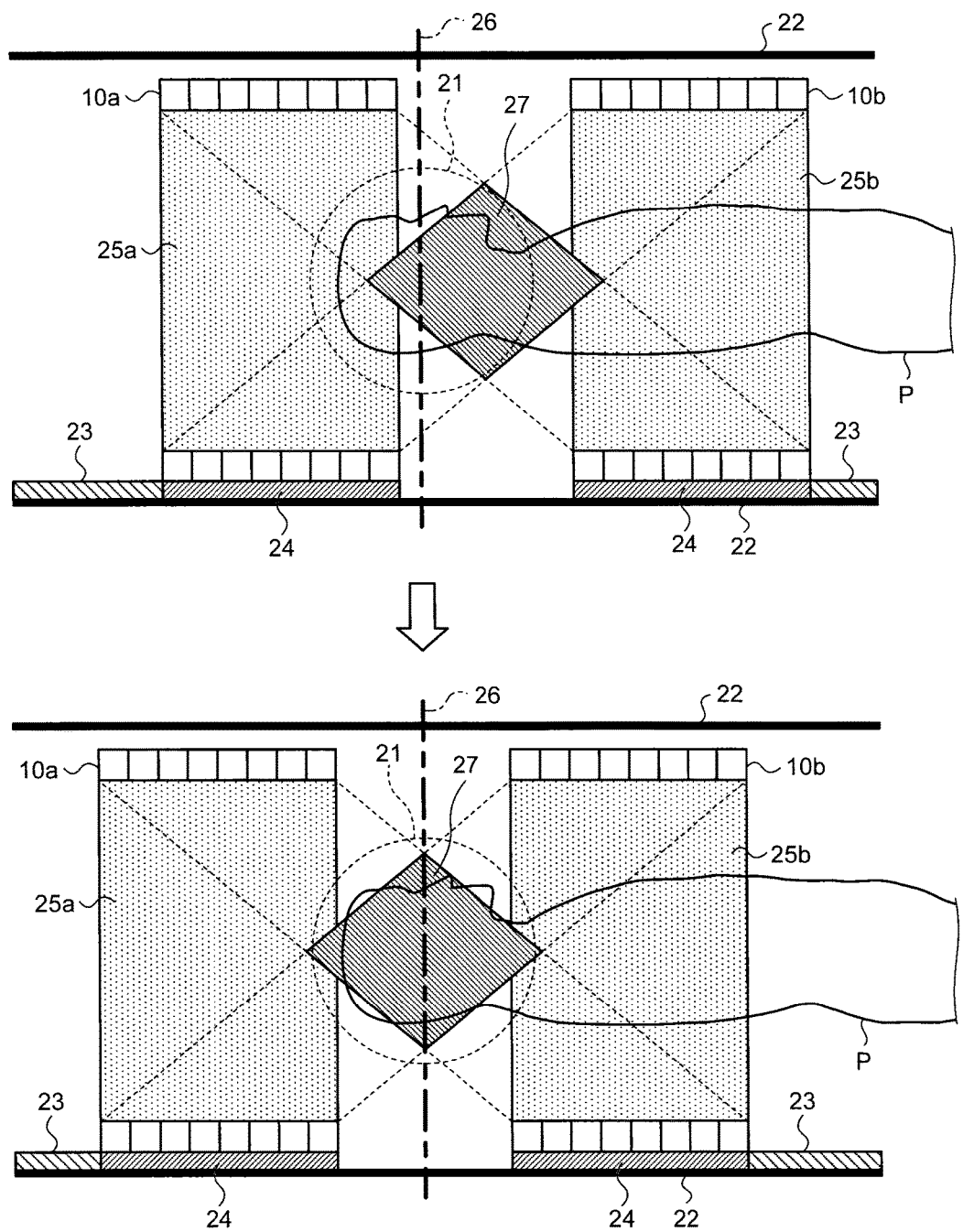
FIG. 8 is a view illustrating the arrangement of a subject in a second diagnosis example.
Figure 9:
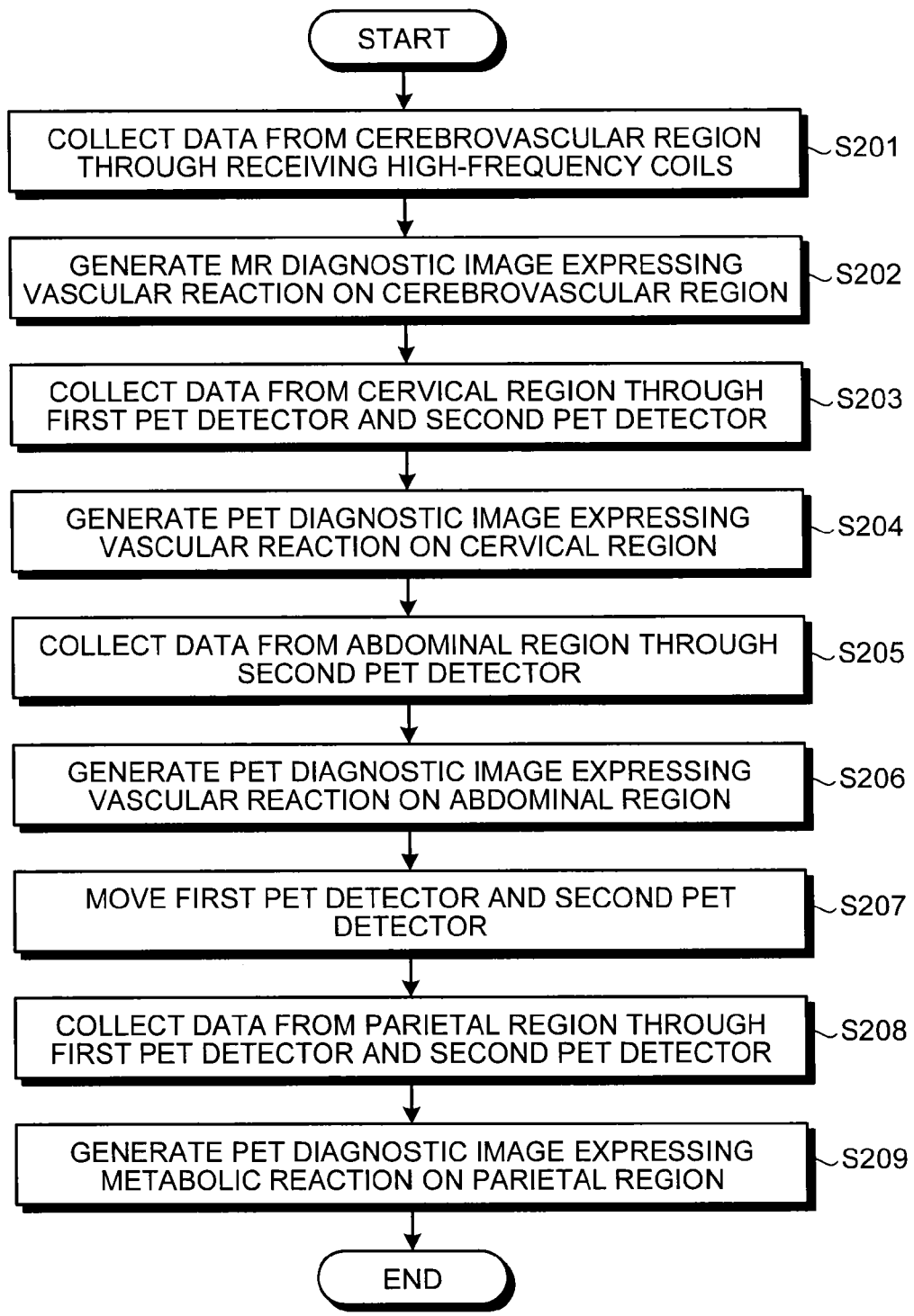
FIG. 9 is a flowchart illustrating the procedure of imaging of diagnostic images in the second diagnosis example.

FIG. 8 is a view illustrating the arrangement of the subject P in the second diagnosis example. FIG. 9 is a flowchart illustrating the procedure of imaging of the diagnostic images in the second diagnosis example. It is to be noted that in the flowchart as illustrated in FIG. 9, the PET detector 10a is expressed as the first PET detector and the PET detector 10b is expressed as the second PET detector.

As illustrated in the upper drawing in FIG. 8, in the second diagnosis example, the subject P is arranged on the PET-MRI device 100 in the same manner as the state as illustrated in FIG. 6 first.

As illustrated in FIG. 9, first, the MR data collector 9 collects data from the cerebrovascular region through the receiving high-frequency coil 7 (step S201). Then, the image generator 16d generates an MR diagnostic image expressing the vascular reaction on the cerebrovascular region from the data collected by the MR data collector 9 (step S202). For example, the image generator 16d generates an MRA image. With this, the operator can observe the vascular reaction on the cerebrovascular region.

Furthermore, the PET data collector 12 collects data from the cervical region through the PET detectors 10a and 10b (step S203). Then, the image generator 16d generates a PET diagnostic image expressing the vascular reaction on the cervical region from the data collected by the PET data collector 12 (step S204). With this, the operator can observe the vascular reaction on the cervical region.

Moreover, the PET data collector 12 collects data from the abdominal region through the PET detector 10b (step S205). Then, the image generator 16d generates a PET diagnostic image expressing the vascular reaction on the abdominal region from the data collected by the PET data collector 12 (step S206). With this, the operator can observe the vascular reaction on the abdominal region.

Thereafter, the detector controller 16b moves the PET detector 10a and the PET detector 10b in the direction from the feet to the head of the subject P (step S207). With this movement, as illustrated in the lower drawing in FIG. 8, the subject P is arranged such that the head region is included in the third PET imaging region 27.

Subsequently, the PET data collector 12 collects data from the head region through the PET detectors 10a and 10b (step S208). Then, the image generator 16d generates a PET diagnostic image expressing the metabolic reaction on the head region from the data collected by the PET data collector 12 (step S209). With this, the operator can observe the metabolic reaction on the head region.

Thus, in the second diagnosis example, first, the diagnostic images for observing the vascular reactions on the cerebrovascular region, the cervical region, and the abdominal region are generated, and then, the PET detectors 10a and 10b are moved. Thereafter, the diagnostic image for observing the metabolic reaction on the head region is generated. The collection controller 16a controls the above-mentioned operations of the MR data collector 9 and the PET data collector 12. The MR data collector 9 and the PET data collector 12 may start data collection at the same time or may start data collection at different timings.

Next, as a third diagnosis example, described is the case where the vascular reaction on the cerebrovascular region is observed with the MR diagnostic image, the vascular reactions on the cervical region and the abdominal region are observed with the PET diagnostic images, and the metabolic reactions on the cardiac region and the head region are observed with the PET diagnostic images.

Figure 10:
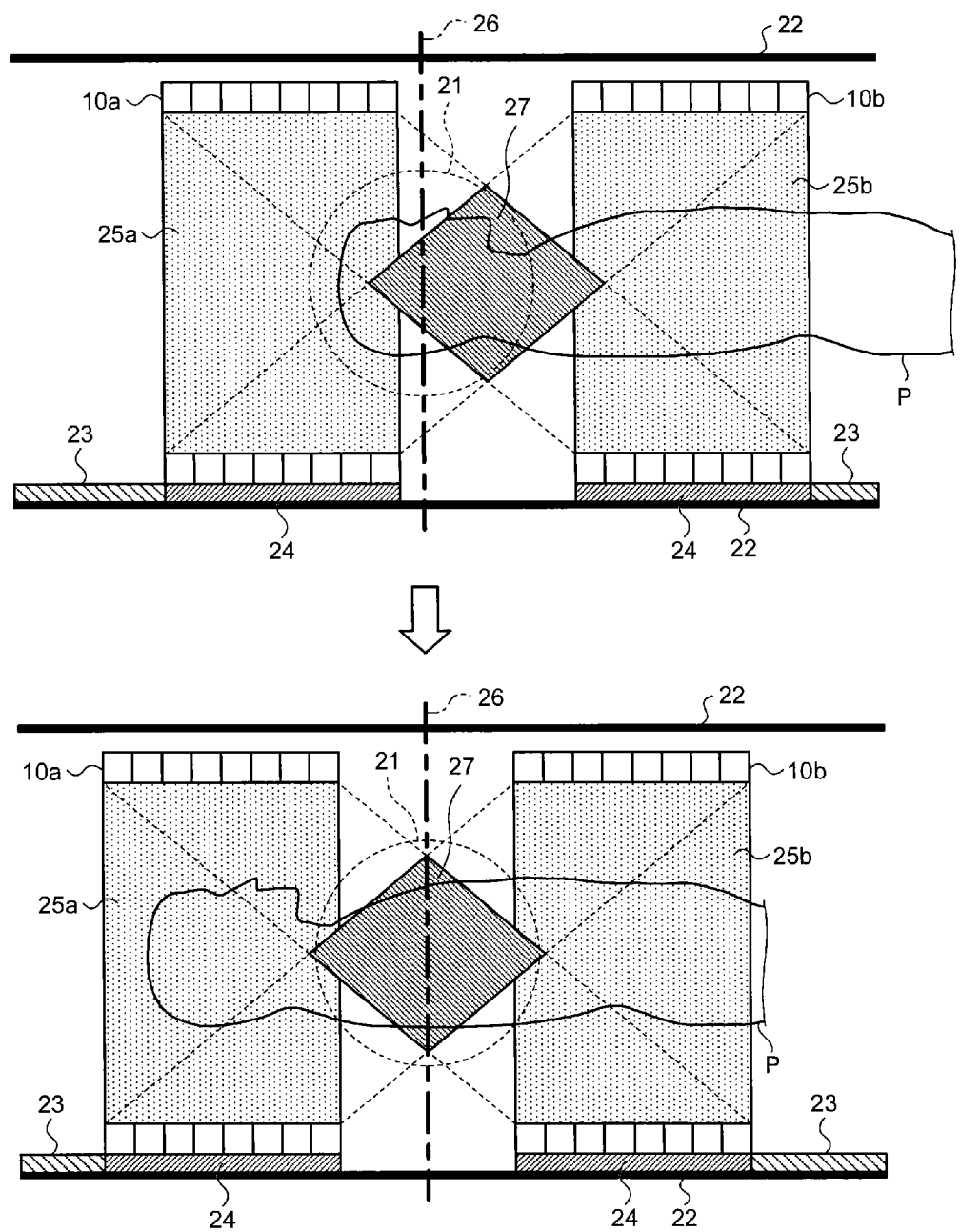
FIG. 10 is a view illustrating the arrangement of a subject in a third diagnosis example.
Figure 11:
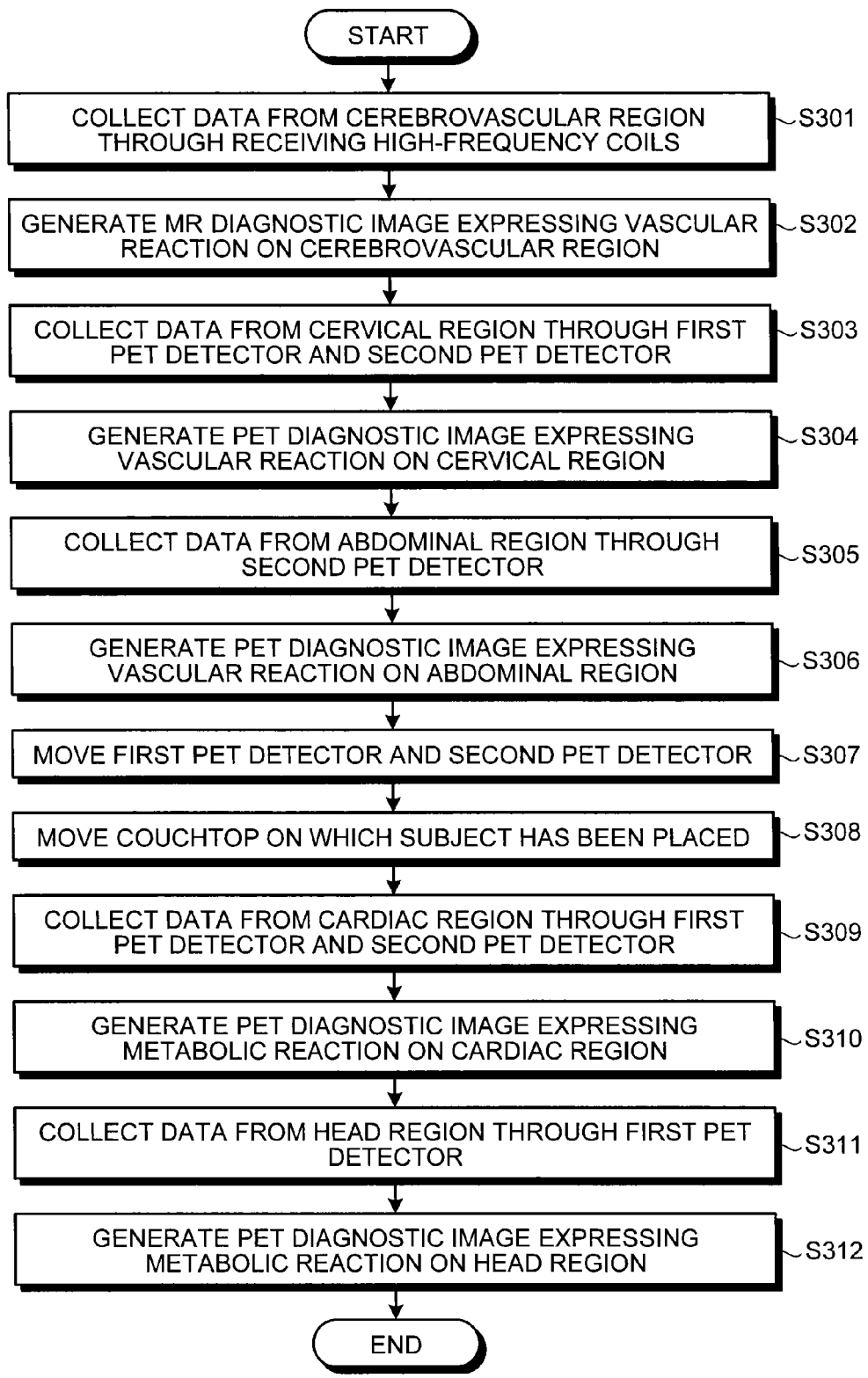
FIG. 11 is a flowchart illustrating the procedure of imaging of diagnostic images in the third diagnosis example.

FIG. 10 is a view illustrating the arrangement of the subject P in the third diagnosis example. FIG. 11 is a flowchart illustrating the procedure of imaging of the diagnostic images in the third diagnosis example. In the flowchart as illustrated in FIG. 11, the PET detector 10a is expressed as the first PET detector and the PET detector 10b is expressed as the second PET detector.

As illustrated in the upper drawing in FIG. 10, in the third diagnosis example, the subject P is arranged on the PET-MRI device 100 in the same manner as the state as illustrated in FIG. 6 first.

As illustrated in FIG. 11, first, the MR data collector 9 collects data from the cerebrovascular region through the receiving high-frequency coil 7 (step S301). Then, the image generator 16d generates an MR diagnostic image expressing the vascular reaction on the cerebrovascular region from the data collected by the MR data collector 9 (step S302). For example, the image generator 16d generates an MRA image. With this, the operator can observe the vascular reaction on the cerebrovascular region.

Then, the PET data collector 12 collects data from the cervical region through the PET detectors 10a and 10b (step S303). Then, the image generator 16d generates a PET diagnostic image expressing the vascular reaction on the cervical region from the data collected by the PET data collector 12 (step S304). With this, the operator can observe the vascular reaction on the cervical region.

Furthermore, the PET data collector 12 collects data from the abdominal region through the PET detector 10b (step S305). Then, the image generator 16d generates a PET diagnostic image expressing the vascular reaction on the abdominal region from the data collected by the PET data collector 12 (step S306). With this, the operator can observe the vascular reaction on the abdominal region.

Thereafter, the detector controller 16b moves the PET detector 10a and the PET detector 10b in the direction from the feet to the head of the subject P (step S307). Furthermore, the couch controller 16c controls the couch 2 to move the couchtop 2a on which the subject P has been placed in the direction from the feet to the head of the subject P (step S308). With this, as illustrated in the lower drawing in FIG. 10, the subject P is arranged such that the head region is included in the first PET imaging region 25a and the cardiac region is included in the third PET imaging region 27.

Subsequently, the PET data collector 12 collects data from the cardiac region through the PET detectors 10a and 10b (step S309). Then, the image generator 16d generates a PET diagnostic image expressing the metabolic reaction on the cardiac region from the data collected by the PET data collector 12 (step S310). With this, the operator can observe the metabolic reaction on the cardiac region.

Furthermore, the PET data collector 12 collects data from the head region through the PET detector 10a (step S311). Then, the image generator 16d generates a PET diagnostic image expressing the metabolic reaction on the head region from the data collected by the PET data collector 12 (step S312). With this, the operator can observe the metabolic reaction on the head region.

Thus, in the third diagnosis example, first, the diagnostic images for observing the vascular reactions on the cerebrovascular region, the cervical region, and the abdominal region are generated, and then, the PET detectors 10a and 10b and the couchtop 2a are moved. Thereafter, the diagnostic images for observing the metabolic reactions on the cardiac region and the head region are generated. The collection controller 16a controls the above-mentioned operations of the MR data collector 9 and the PET data collector 12. The MR data collector 9 and the PET data collector 12 may start data collection at the same time or may start data collection at different timings.

In the above-mentioned first to third diagnosis examples, described have been the cases where pieces of data relating to the vascular reaction and the metabolic reaction are collected. The vascular reaction indicates increase in the capillary vessels and increase in the blood flow around a lesion site when inflammation at the lesion site progresses, for example. The vascular reaction can be observed with a perfusion image or the like. The metabolic reaction indicates activation of metabolism of cells and tissues when abnormality is generated on the cells and the tissues. The lesion site takes isotopic elements injected to the subject or labeled compounds thereof with the metabolic reaction. A PET image indicating dose distribution of gamma rays is obtained by measuring the gamma rays emitted from the isotopic elements or the labeled compounds thereof.

In the medical image diagnostic device according to the above-mentioned embodiment, reaction to be diagnosed is not limited thereto. For example, the medical image diagnostic device may collect data relating to drug reaction. Note that the drug reaction herein indicates specific reaction generated by a specific drug when abnormality is generated on the cells and the tissues. A drug is selected in accordance with the cells and the tissues to be diagnosed and the drug is injected to the subject. Then, if the drug bonds to abnormal cells and tissues, the cells and the tissues can be imaged as the PET image or the MR image by contrast enhancement of the drug.

As for the flows of the imaging as described in the above-mentioned first to third diagnosis examples, the operator sets imaging regions as targets and the imaging order in advance. In this case, for example, the console 17 accepts imaging conditions including at least the respective imaging regions and the timings at which data is collected from the respective imaging regions from the operator. Then, the collection controller 16a controls the MR data collector 9 and the PET data collector 12 in accordance with the imaging conditions received by the console 17.

For example, the console 17 further accepts a type of a contrast agent or a drug to be injected to the subject, a waiting time until the data is collected since the contrast agent or the drug was injected, and the like in addition to the respective imaging regions and the timings at which data is collected from the respective imaging regions from the operator. The waiting time herein indicates time at which the vascular reaction reaches a peak since the contrast agent was injected to the subject, time at which the metabolic reaction reaches a peak since the drug was injected to the subject, or the like. In this case, for example, when data collection by using the contrast agent or the drug and data collection without using the contrast agent or the drug are performed, the collection controller 16a determines an execution timing of the data collection by using the contrast agent or the drug based on the waiting time until the data is collected since the contrast agent or the drug was injected while putting it ahead of the data collection without using the contrast agent or the drug.

As described above, according to the first embodiment, the MR diagnostic image or the PET diagnostic image can be generated for each lesion site of equal to or more than one lesion site in the subject.

Figure 12:
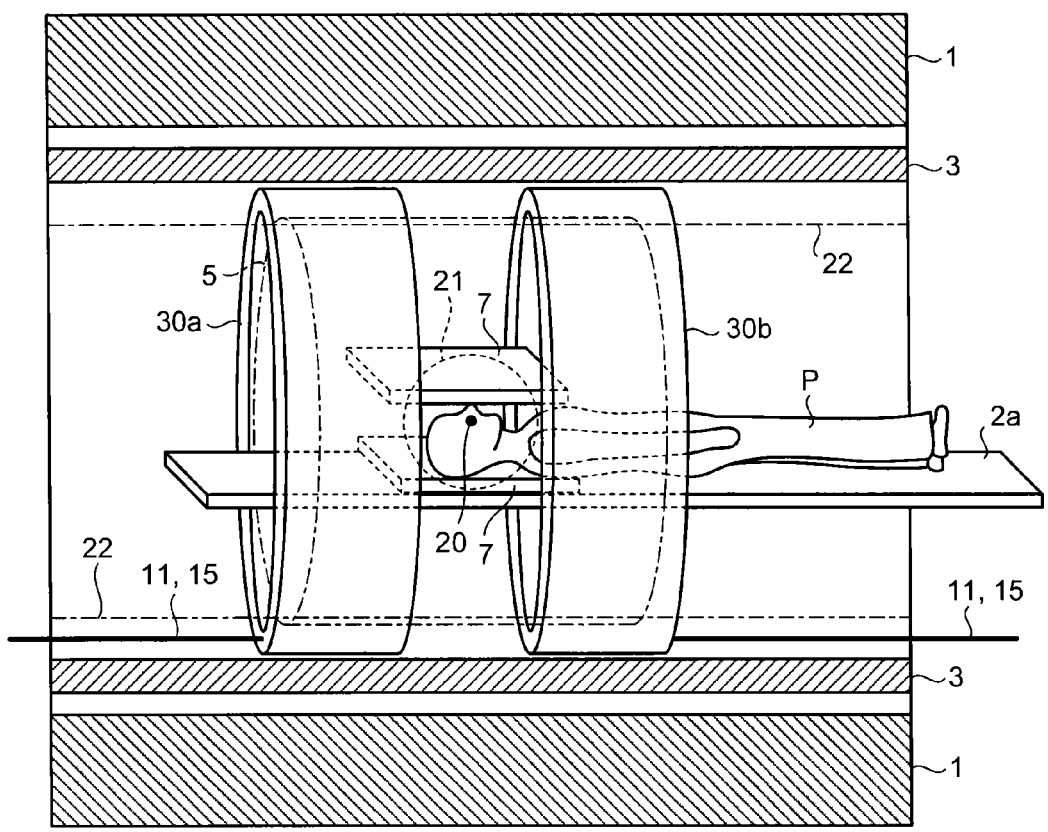
FIG. 12 is a view illustrating another example relating to the arrangement of the PET detectors in the first embodiment.

Although described has been the case where the PET detectors are provided at the inner circumferential side of the transmitting high-frequency coil 5 as an example in the embodiment, arrangement of the PET detectors is not limited thereto. FIG. 12 is a view illustrating another example relating to the arrangement of the PET detectors according to the first embodiment. As illustrated in FIG. 12, for example, PET detectors 30a and 30b may be provided at the outer circumferential side of the transmitting high-frequency coil 5.

For example, the PET detectors 30a and 30b are provided in a space between the transmitting high-frequency coil 5 and the gradient coil 3 so as to be movable in the axial direction of the bore. The configuration is used, for example, when the body part is imaged and when a whole-body transmitting high-frequency coil is used as the transmitting high-frequency coil 5 and a body part-dedicated surface coil is used as the receiving high-frequency coil 7.

Second Embodiment

Figure 13:
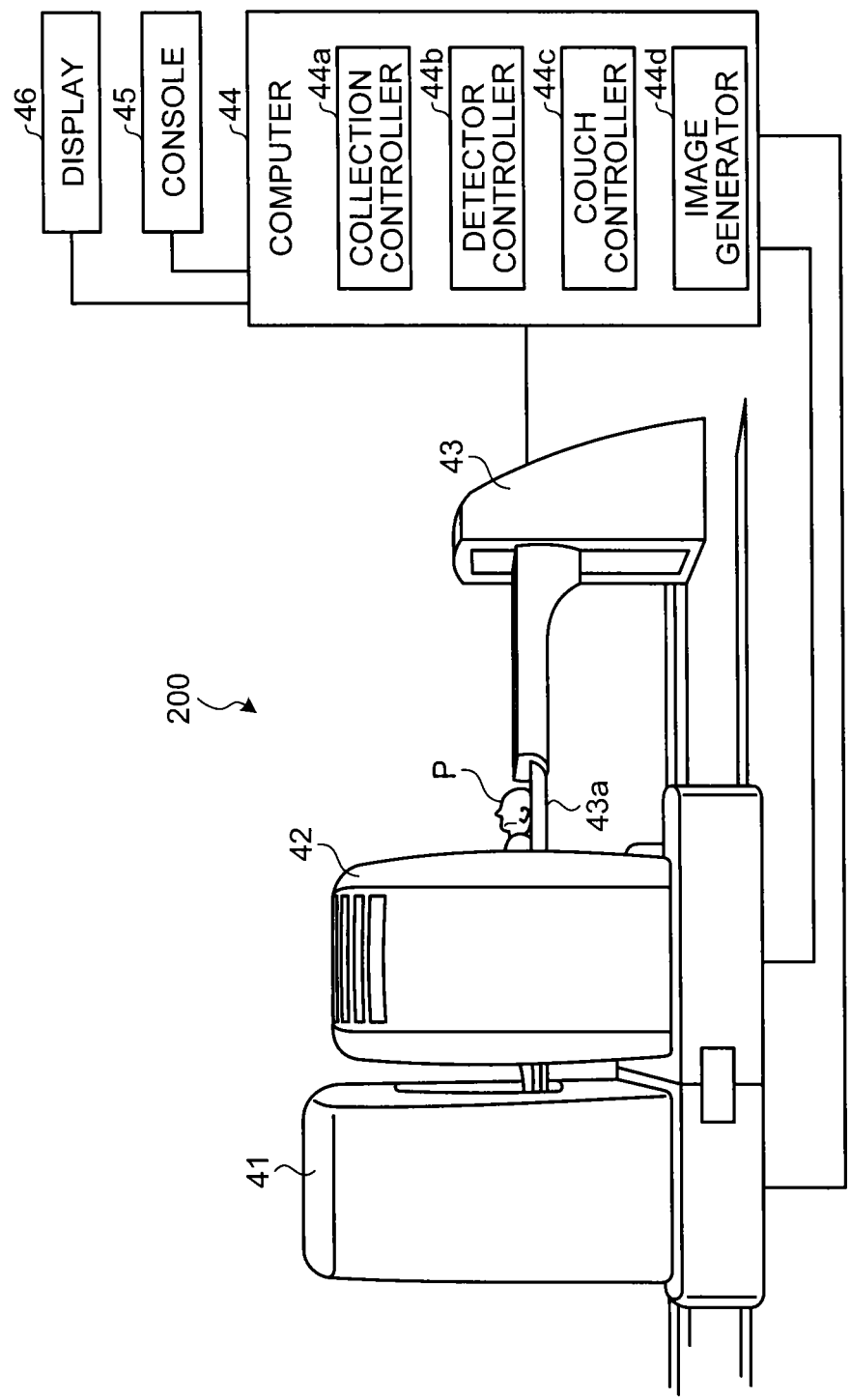
FIG. 13 is a view illustrating a configuration of a PET-CT device according to a second embodiment.

Next, described is a second embodiment. FIG. 13 is a view illustrating a configuration of a PET-CT device according to the second embodiment. As illustrated in FIG. 13, a PET-CT device 200 according to the second embodiment includes a PET gantry device 41, a CT gantry device 42, a couch 43 and a computer 44.

The PET gantry device 41 detects a pair of gamma rays emitted from the tissue that has taken the positron-emitting radionuclide administered to the subject P so as to generate gamma ray projected data for reconstructing a PET image.

Figure 14:
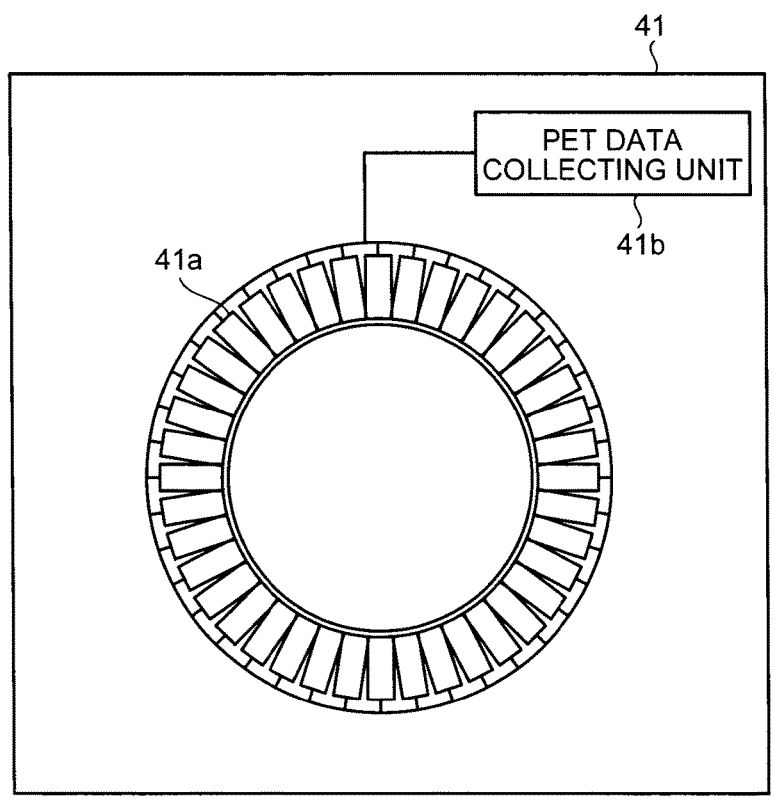
FIG. 14 is a view illustrating a configuration of a PET gantry device in the second embodiment.

FIG. 14 is a view illustrating a configuration of the PET gantry device 41 in the second embodiment. As illustrated in FIG. 14, the PET gantry device 41 includes a plurality of PET detector modules 41a constituting a PET detector and a PET data collector 41b.

The PET detector modules 41a are photon counting detectors that detect gamma rays emitted from the subject P, for example. The PET detector is constituted by arranging the PET detector modules 41a so as to surround the subject P in a ring form. For example, each of the PET detector modules 41a is an Anger-type detector including scintillators, photomultiplier tubes (PMT), and a light guide.

The scintillators are constituted by two-dimensionally arranging a plurality of sodium iodide (NaI), bismuth germinate (BGO), lutetium yttrium oxyorthosilicate (LYSO), lutetium oxyorthosilicate (LSO), lutetium gadolinium oxyorthosilicate (LGSO), and the like for converting the gamma rays that have been emitted from the subject P and entered the scintillators into visible light. The photomultiplier tubes are devices for multiplying the visible light output from the scintillators and converting it into an electric signal. A plurality of photomultipliers are densely arranged through the light guide. The light guide is used for transmitting the visible light output from the scintillators to the photomultipliers and is made of a plastic material excellent in light transmissivity.

The PET data collector 41b collects coincidence data through the PET detector. To be more specific, the PET data collector 41b generates combined data of pieces of count information obtained by detecting the gamma rays (including annihilation radiation) emitted from the positron-emitting radionuclide at substantially the same time by using the pieces of count information of the gamma rays detected by the PET detector so as to collect the coincidence data.

The CT gantry device 42 is a device that detects X rays through the subject P so as to generate X-ray projected data for reconstructing an X-ray CT image and X-ray projected data for generating a scanogram to be used for making an imaging plan.

Figure 15:
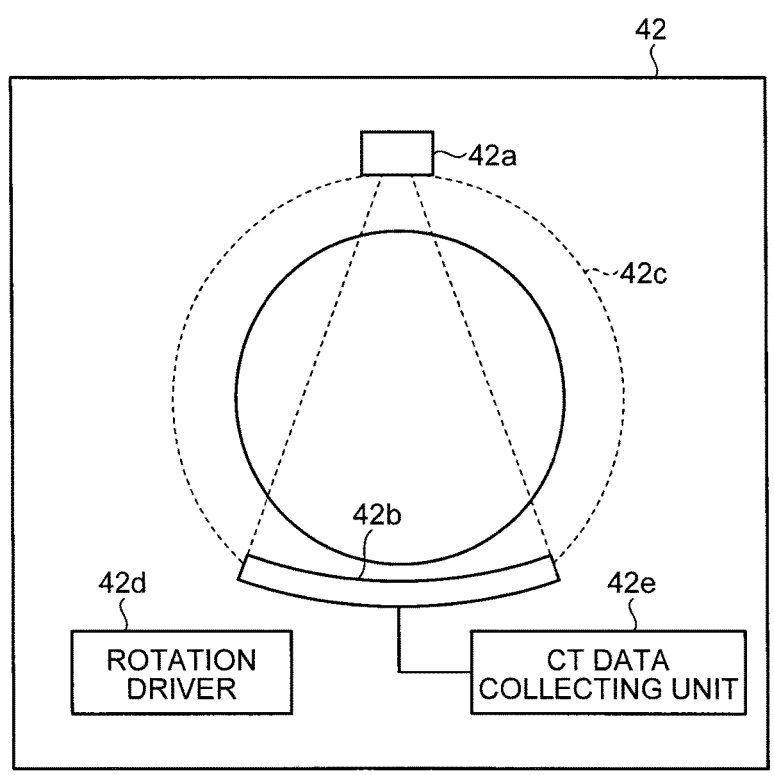
FIG. 15 is a view illustrating a configuration of a CT gantry device in the second embodiment.

FIG. 15 is a view illustrating a configuration of the CT gantry device 42 in the second embodiment. As illustrated in FIG. 15, the CT gantry device 42 includes an X-ray tube 42a, an X-ray detector 42b, a rotating frame 42c, a rotation driver 42d and a CT data collector 42e.

The X-ray tube 42a generates X rays and irradiates the subject P with the X rays. The X-ray detector 42b is arranged at a position opposite to the X-ray tube 42a and detects the X rays through the subject P. To be more specific, the X-ray detector 42b detects data of two-dimensional intensity distribution of X rays (two-dimensional X-ray intensity distribution data) through the subject P. The rotating frame 42c supports the X-ray tube 42a and the X-ray detector 42b at opposite positions.

The rotation driver 42d rotates the X-ray tube 42a and the X-ray detector 42b substantially about the subject P. To be more specific, the rotation driver 42d rotates the rotating frame 42c supporting the X-ray tube 42a and the X-ray detector 42b substantially about the subject P.

The CT data collector 42e acquires the two-dimensional intensity distribution data detected by the X-ray detector 42b. Then, the CT data collector 42e performs amplification processing and A-to-D conversion processing on the acquired two-dimensional intensity distribution data so as to collect X-ray projected data.

Returning to the explanation of FIG. 13, the couch 43 includes a couchtop 43a on which the subject P is placed. The couch 43 moves the couchtop 43a to the inner side of openings for imaging included in the PET gantry device 41 and the CT gantry device 42 at the time of the imaging.

The computer 44 controls the overall PET-CT device 200. The computer 44 includes a console 45 and a display 46. The console 45 accepts various types of operations from an operator. The display 46 displays various types of information such as a medical image and a GUI. The computer 44 includes a central processing unit (CPU) and a memory that execute various types of programs so as to execute various types of processing. Furthermore, the computer 44 includes a collection controller 44a, a detector controller 44b, a couch controller 44c, and an image generator 44d. These functional units are operated by executing various types of programs on the above-mentioned CPU and memory.

The collection controller 44a controls the PET data collector 41b and the CT data collector 42e in accordance with a direction from the operator. For example, the collection controller 44a controls the PET data collector 41b and the CT data collector 42e so as to start data collection at the same time. Alternatively, for example, the collection controller 44a controls them such that the CT data collector 42e starts data collection after a predetermined time has elapsed since the PET data collector 41b started data collection.

The detector controller 44b controls the movement of the PET detector and the X-ray detector 42b. To be more specific, the detector controller 44b moves the PET detector in an axial direction of the opening included in the PET gantry device 41. Furthermore, the detector controller 44b moves the X-ray detector 42b in an axial direction of the opening included in the CT gantry device 42.

The couch controller 44c controls the operation of the couch 43 on which the subject P is placed. For example, the couch controller 44c controls the couch 43 so as to move the couchtop 43a on which the subject P is placed in the axial direction of the openings included in the PET gantry device 41 and the CT gantry device 42.

The image generator 44d generates a PET diagnostic image from the coincidence data collected by the PET data collector 41b and generates a CT diagnostic image from the X-ray projected data collected by the CT data collector 42e. Then, the image generator 44d displays the generated PET diagnostic image and the generated CT diagnostic image on the display 46.

For example, the image generator 44d generates a functional image such as a metabolic imaging image and a molecular imaging image as the PET diagnostic image. For example, the image generator 44d generates a morphological image such as a CT angiography (CTA) image and a digital subtraction angiography (DSA) image or a functional image such as a perfusion image as the CT diagnostic image.

In this manner, the image generator 16d generates various types of diagnostic images so as to generate a diagnostic image suitable to diagnosis of each lesion site of equal to or more than one lesion site in the subject P. The diagnosis herein indicates observation of vascular reaction and metabolic reaction on the lesion site, for example. For example, the vascular reaction can be observed by using the morphological image as the diagnostic image. Furthermore, the metabolic reaction can be observed by using the functional image as the diagnostic image.

The procedure of the imaging of the diagnostic images by the PET-CT device 200 according to the second embodiment is basically the same as the procedure of the imaging of the diagnostic images by the PET-MRI device 100 as described above with reference to FIGS. 6 to 11, and only the type of the detector and the type of the diagnostic images are different. That is to say, the PET diagnostic image or the CT diagnostic image is generated for each of the different regions of the subject P in the second embodiment. An operator can observe the vascular reaction and the metabolic reaction for each lesion site by observing the generated diagnostic images.

As described above, according to the second embodiment, the PET diagnostic image or the CT diagnostic image can be generated for each lesion site of equal to or more than one lesion site in the subject.

Although the PET-MRI device and the PET-CT device have been described in the above-mentioned embodiments, embodiments of the medical image diagnostic device are not limited thereto. For example, a technique disclosed by the present application can be also executed by a PET device including at least two PET detectors.

In this case, the PET device includes a first PET detector, a second PET detector, a first collector, a second collector, and an image generator. The first PET detector and the second PET detector each detect gamma rays to be emitted from the positron-emitting radionuclide administered to the subject. Furthermore, the first collector collects data from a first region of the subject through the first detector. The second collector collects data from a second region of the subject that is different from the first region through the second detector. The image generator generates a first PET diagnostic image from the data collected by the first collector and generates a second PET diagnostic image from the data collected by the second collector.

The procedure of the imaging of the diagnostic images by the above-mentioned PET device is basically the same as the procedure of the imaging of the diagnostic images by the PET-MRI device 100 as described above with reference to FIGS. 6 to 11, and only the type of the detectors and the type of the diagnostic images are different. That is to say, the above-mentioned PET device generates a PET diagnostic image for each of the different regions of the subject P. An operator can observe the vascular reaction and the metabolic reaction on each lesion site by observing the generated diagnostic images.

With the respective embodiments as described above, the diagnostic image can be generated for each lesion site of equal to or more than one lesion site in the subject.

Although some embodiments of the invention have been described above, these embodiments are presented by way of example only, and are not intended to limit the scope of the invention. These embodiments can be executed in a variety of other forms. Various omissions, substitutions, and changes can be made without departing from the spirit of the invention. These embodiments and modifications thereof are covered by the scope and spirit of the invention and fall within the scope of the invention set forth in the accompanying claims and equivalents thereof.

What is claimed is:

1. A PET (Positron Emission Tomography)-MRI (Magnetic Resonance Imaging) apparatus, comprising:

a static magnetic field magnet accommodated in a gantry in which a bore is formed, the static magnetic field magnet being configured to generate a static magnetic field;

a gradient coil arranged at an inner circumferential side of the static magnetic field magnet, the gradient coil being configured to generate a gradient magnetic field;

a high-frequency coil arranged at an inner circumferential side of the gradient coil, the high-frequency coil being configured to apply a high-frequency magnetic field to a subject;

a first detector and a second detector each arranged at an inner circumferential side of the gradient coil, the first and the second detectors each having a substantially same shape and being configured to detect gamma rays emitted from the subject, wherein the first and the second detectors detect the gamma rays in a state that the first and the second detectors are spaced apart in an axial direction of the bore such that the first and second detectors are spaced on opposite sides of center of the static magnetic field with the space therebetween encompassing the center of the static magnetic field and are disposed asymmetrically with respect to the center of the static magnetic field.

2. The PET-MRI apparatus according to claim 1, further comprising:

a first collector that collects data from a first region of a subject through the high-frequency coil;

a second collector that collects data from a second region of the subject that is different from the first region through the first and the second detectors; and an image generator that generates a first diagnostic image from the data collected by the first collector and generates a second diagnostic image from the data collected by the second collector.

3. The PET-MRI apparatus according to claim 2, further comprising a collection controller that controls the first and the second collectors to start data collection at a same time.

4. The PET-MRI apparatus according to claim 2, further comprising a collection controller that controls the first and the second collectors such that one of the first and the second collectors starts data collection after a predetermined time has elapsed since the other of the first and the second collectors started data collection.

5. The PET-MRI apparatus according to claim 4, further comprising a detector controller that moves the first and the second detectors after the first and the second collectors have finished data collection, wherein the second collector collects data from the first region through the first and the second detectors after the first and the second detectors have been moved.

6. The PET-MRI apparatus according to claim 4, further comprising a detector controller that moves the first and the second detectors after the first and the second collectors have finished data collection, wherein the second collector collects data from a third region different from the first and the second regions through the first and the second detectors after the first and the second detectors have been moved.

7. The PET-MRI apparatus according to claim 4, further comprising a couch controller that controls a couch on which the subject is placed to move the subject after the first and the second collectors have finished data collection, wherein the second collector collects data from the first region through the first and the second detectors after the subject has been moved.

8. The PET-MRI apparatus according to claim 4, further comprising a couch controller that controls a couch on which the subject is placed to move the subject after the first and the second collectors have finished data collection, wherein the second collector collects data from a third region different from the first and the second regions through the first and the second detectors after the subject has been moved.

9. The PET-MRI apparatus according to claim 2, wherein the first collector collects data relating to first reaction of the subject from the first region, and the second collector collects data relating to second reaction of the subject that is different from the first reaction from the second region.

10. The PET-MRI apparatus according to claim 2, wherein a part of the first region and a part of the second region are overlapped.

11. The PET-MRI apparatus according to claim 2, further comprising:

an acceptor that accepts imaging conditions including at least the first region, the second region, a timing at which data is collected from the first region, and a timing at which data is collected from the second region from an operator, and a collection controller that controls the first and the second collectors in accordance with the imaging conditions.

* * * * *